United States Patent [19]

Cohen

[11] Patent Number: 4,739,752
[45] Date of Patent: Apr. 26, 1988

[54] DISPOSABLE COVER FOR PRESSURE TROUSERS

[76] Inventor: Mark Cohen, 1533 NW. 111th Ave., Coral Springs, Fla. 33065

[21] Appl. No.: 40,119

[22] Filed: Apr. 20, 1987

[51] Int. Cl.[4] ................................................ A61F 5/34
[52] U.S. Cl. ................................ 128/132 R; 128/133; 128/DIG. 20
[58] Field of Search ............... 128/87 R, 89 R, 132 R, 128/133, 134, 24 R, 60, DIG. 15, DIG. 20, 132 D; 2/46, 231, 232

[56] References Cited

U.S. PATENT DOCUMENTS

| | | | |
|---|---|---|---|
| 2,763,264 | 9/1956 | McInnerny | 128/133 |
| 4,182,320 | 1/1980 | Sweeney | 128/DIG. 20 X |
| 4,406,281 | 9/1983 | Hubbard et al. | 128/132 R |
| 4,509,213 | 4/1985 | Harvey | 2/231 X |

Primary Examiner—Robert A. Hafer
Assistant Examiner—K. G. Rooney
Attorney, Agent, or Firm—Alvin S. Blum

[57] ABSTRACT

A disposable plastic cover for inflatable anti-shock trousers prevents contamination of the trousers in use. The trousers need not be washed or decontaminated between uses. The cover engages the trousers firmly on the inside and provides the same securing means on its outer surfaces for holding tightly around the patient when the trousers are inflated to pressurize the lower body to prevent shock.

16 Claims, 3 Drawing Sheets

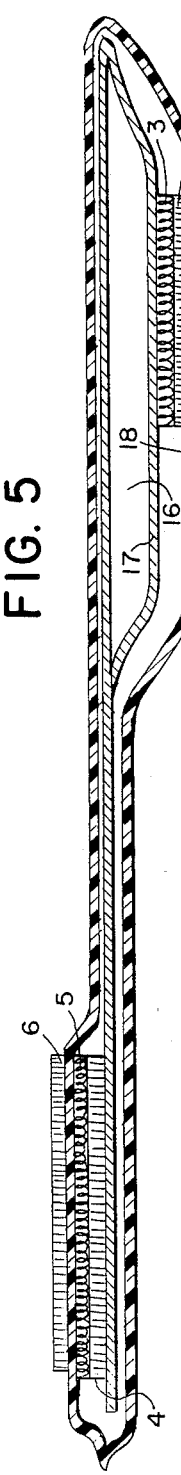
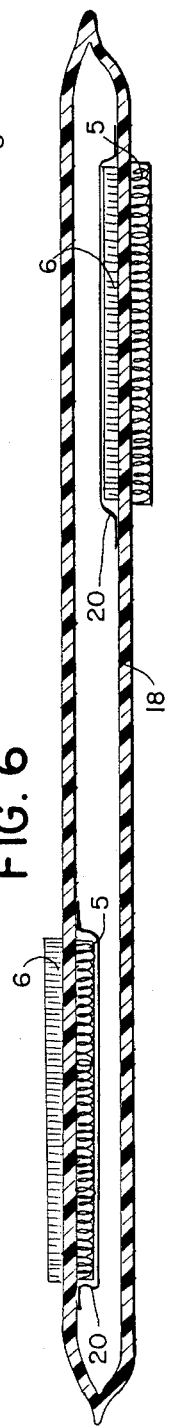
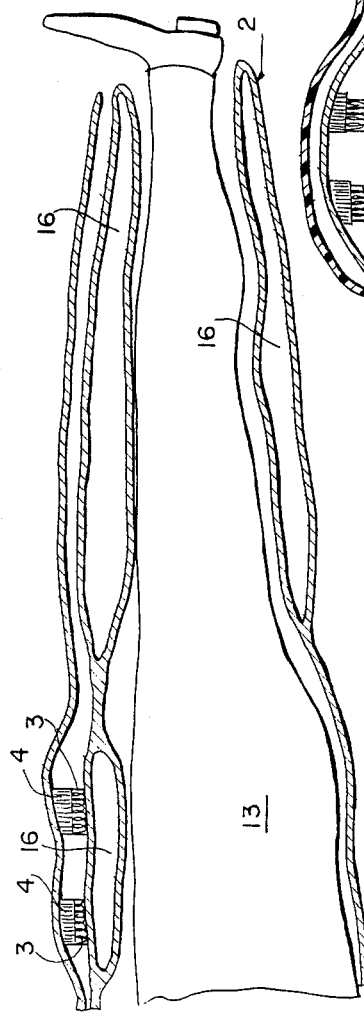
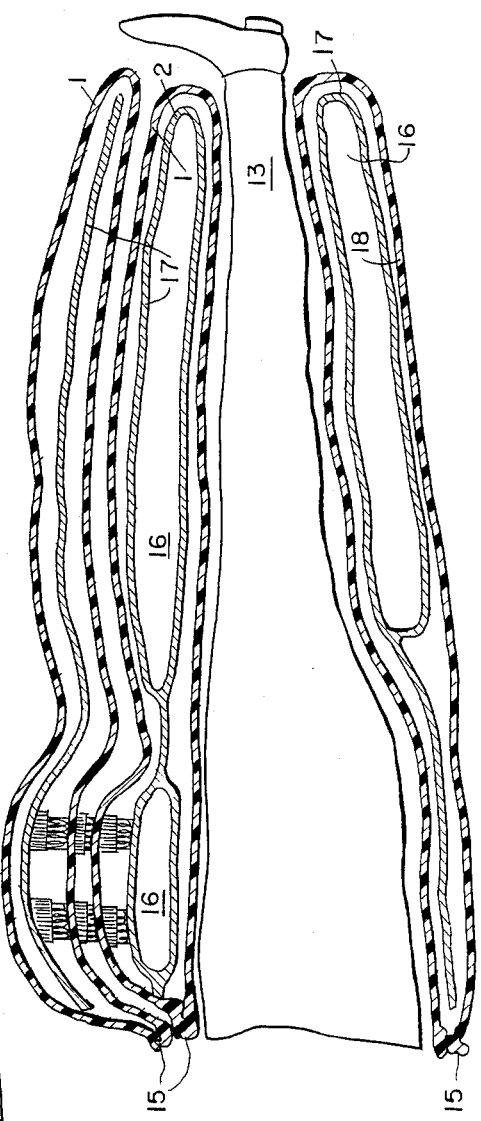

DISPOSABLE COVER FOR PRESSURE TROUSERS

This invention relates to inflatable pressure trousers used for maintaining blood pressure in emergencies and more particularly to disposable covers for such trousers.

BACKGROUND OF THE INVENTION

When persons are in shock or have lost considerable amounts of body fluids, especially blood, circulatory dynamics may be so impaired that there is insufficient perfusion of the brain by the circulating blood. Such a condition deprives the brain of oxygen and can lead to the permanent injury of brain tissue or death within minutes. This situation is often encountered by emergency medical services at the scene of an accident and by military medical units in the field. To overcome the problem, a number of devices have been developed for compressing the legs and abdomen to force more blood to the upper body. U.S. Pat. Nos. 3,933,150; 4,039,039; 4,270,527 and 4,531,516 describe inflatable trouser-like garments, generally referred to as anti-shock trousers or air pants, that have been quite successful and are in wide use in emergency medical services. These devices are designed to open and lie flat upon a surface. The patient is placed on the device and then the leg portions are closed over each leg and the abdominal portion is closed over the abdomen. The trousers are adjustable to various body sizes with "Velcro" fasteners used for closures. After closing the trousers over the lower body, air chambers enclosed within the trousers are inflated to apply a controlled pressure to the lower body to maintain blood pressure.

In practice, these devices are subject to much trauma and contamination from dirt at the accident site, but, more importantly, from the blood, urine and feces of the patient. Because of the dangers of transmission of disease such as the blood born incurable disease AID, and the threat of financial liability, rather elaborate and rigorous cleaning and decontamination procedures are prescribed after every use. The trousers are made of a sturdy fabric that is washable. The air chambers in some models are detachable to spare them the trauma of washing. However, the rigors of the decontamination procedures greatly shorten the life of these expensive devices. They are removed from use awaiting decontamination. And using skilled emergency personnel for washing trousers is also costly.

SUMMARY OF THE INVENTION

It is, accordingly, an object of the invention to provide a means of decontaminating pressure trousers after use that is fast, and less costly than current methods.

It is a further object to protect the pressure trousers from trauma during use. The invention comprises a disposable cover for pressure trousers that is inexpensive, easily replaced, protects the trousers from trauma and contamination and that does not interfere with the use and normal operation of the trousers. These and other objects and advantages of the present invention will become more apparent as the description proceeds with the aid of the accompanying drawings.

BRIEF DESCRIPTION OF THE DRAWINGS

FIG. 5 is a cross section taken on plane 5—5 of FIG. 1.

FIG. 6 is a detail of FIG. 5 with trousers removed and cover strips protecting closures.

FIG. 7 is a longitudinal cross section of the trousers of the prior art in place on a patient.

FIG. 8 is a longitudinal cross section of the device covering the trousers, in place on a patient.

DETAILED DESCRIPTION OF THE PREFERRED EMBODIMENTS

Figure 1:
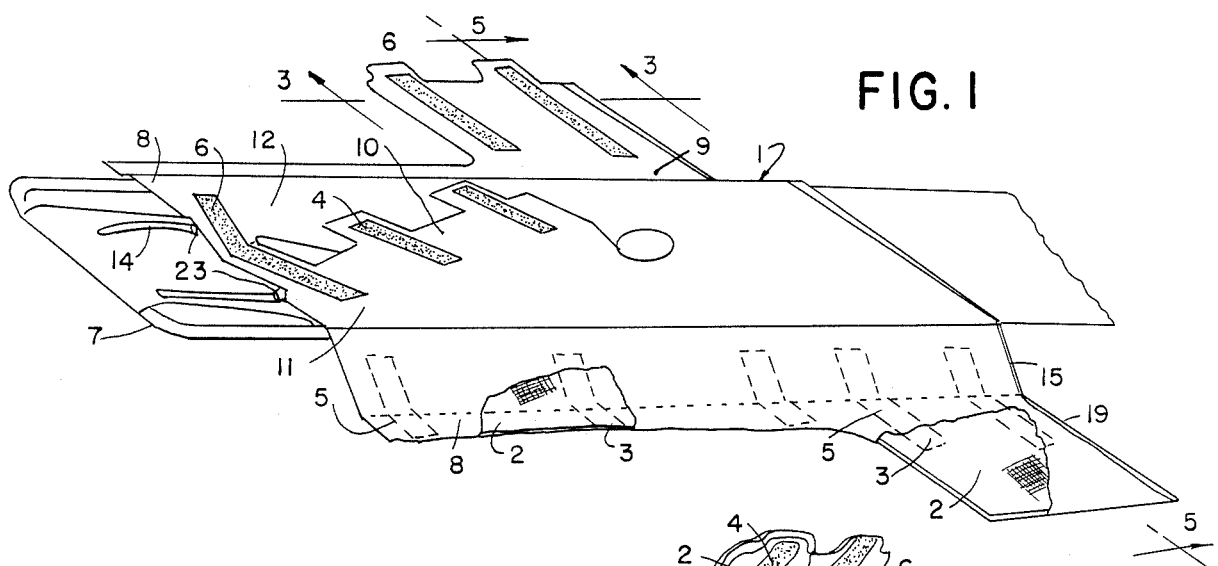
FIG. 1 shows the device in perspective on a stretcher, ready for use, with a portion broken away to show the trousers inside.
Figure 2:
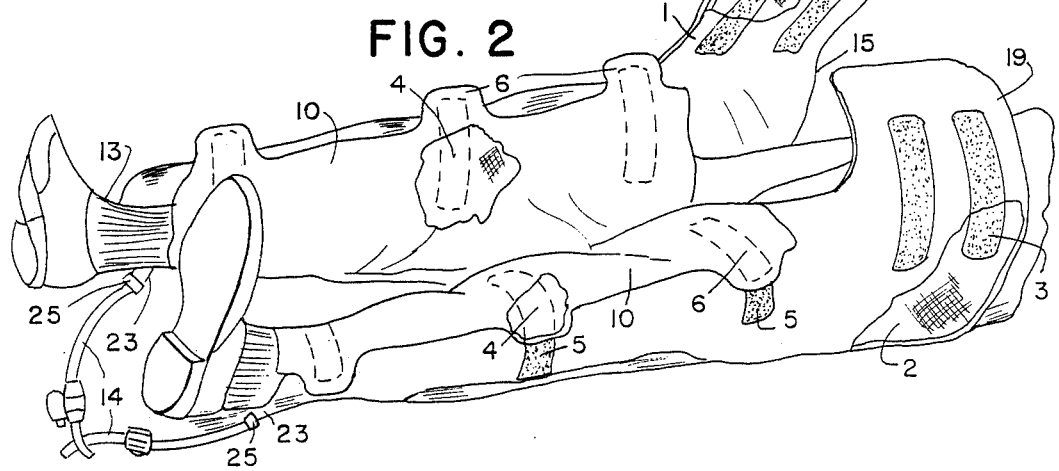
FIG. 2 shows the device in perspective being wrapped around a patient with portions broken away to show the trousers inside.

Referring first to FIGS. 1 and 2, the invention, in the form of a disposable, impermeable, plastic film cover 1, completely encloses the inflatable trousers 2, which are visible where the cover has been broken away. As shown in FIG. 1, the covered trousers are laid out flat on stretcher 7 for use on a patient. Both the leg portions 8 and the abdomen portion 9 are wide enough to provide a wide overlap 10 even in large patients as seen in FIG. 2 where it is being wrapped around the patient 13. The overlapping portion 10 of one leg 11 covers a portion of the second leg 12 when laid out flat as in FIG. 1. The overlapped portions are held securely in place by the adjustable hook and loop fastener strips trademarked "Velcro". After securing the covered garment 1 around the patient 13, the gas chambers in the leg and abdomen portions are inflated with compressed gas through tubes 14. The long strip of loop portions 5 of the cover engage the long strip of hook portions 6 over a wide range of patient size. Where the Velcro strips are on the underside of the cover or trousers, they are indicated by phantom lines in the drawings.

In order for the plastic cover to hold the trousers securely in place around the patient to apply pressure to the body when the chambers are inflated, the trousers must be securely affixed to the cover at those points where the trousers are normally fastened together by the Velcro fasteners. The trouser hook portions 4 and loop portions 3 are shown in FIGS. 1 and 2 where the cover is broken away.

Figure 3:
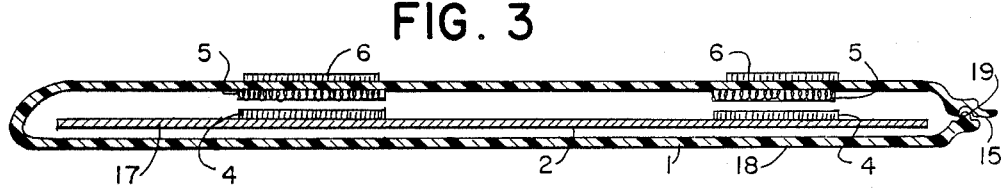
FIG. 3 is a cross section taken on plane 3—3 of FIG. 1.
Figure 4:
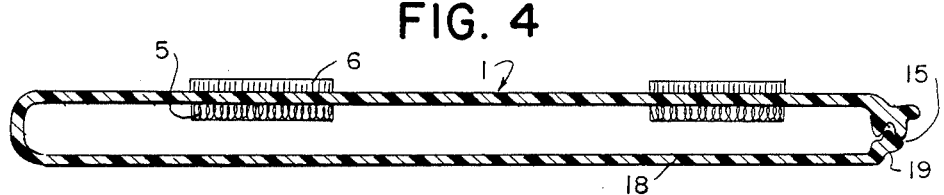
FIG. 4 is a detail of FIG. 3 with trousers removed.

To secure the cover 1 to the trousers 2, the cover is provided with appropriate Velcro fastening strips on its inside surface at each area where a Velcro strip is found on the trousers so that the two may be firmly fixed together before use. The cover is also provided with appropriate Velcro strips on its outer surface at those same locations above the inner Velcro strips so that the overlapping portions of the cover can be secured together in the same manner of operation as the original trousers. This is more clearly seen in the cross sectional views of FIGS. 3,5 and 8. The trousers (FIG. 7) of the prior art are generally made of a coated nylon fabric to hold gas in inflatable chambers 16. The fabric layer 17 of the trousers 2 and the thin sheet (e.g. 0.005 inches) of the disposable plastic film cover 1 are shown much thicker and more spaced apart for illustrative purposes.

The entire upper edge 15 of the cover can be opened for insertion of the trousers for use and removal of the trousers for disposal of the cover after use. A sealable closure is provided for upper edge 15. This may be the trademarked "Ziploc" strip 19 shown, a Velcro fastener, or an adhesive closure.

Figure 9:
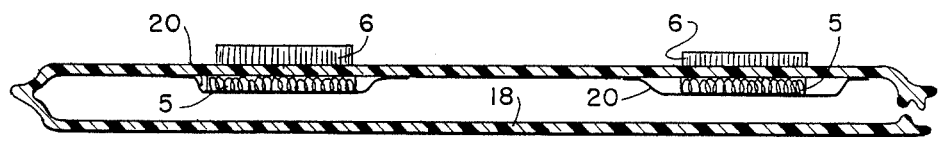
FIG. 9 is a detail of FIG. 4 with cover strips in place covering the closure strips.

When the trousers 2 are inserted into the cover 1, the exposed Velcro fasteners make insertion awkward. To overcome this problem, the Velcro fasteners on the inside of the cover are provided with removable cover strips 20 (FIGS. 6 and 9) that may be stripped off after the trousers are in place in the cover. These cover strips may be matching Velcro strips or adhesive strips that stick to the film adjacent the Velcro as illustrated.

Figure 10:
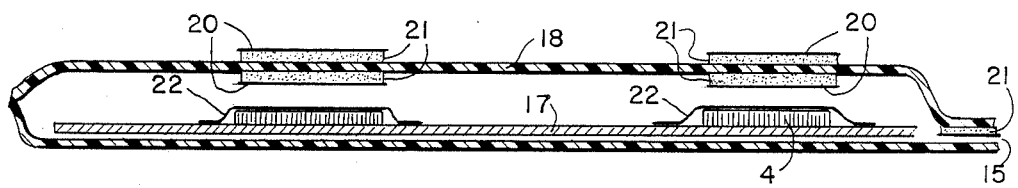
FIG. 10 is a detail of FIG. 3 with cover strips in place covering the alternative adhesive closure strips.

The Velcro closures have been found useful for trousers because they can be resealed many times without loss of effectiveness. However, in the disposable covers of the instant invention, the closures will be used only once and then discarded. Consequently, a less expensive closure may be used such as the pressure sensitive adhesive strips 22 as shown in FIG. 10. The Velcro closures on the trousers may be covered with fabric covers 22 permanently cemented in place on the trousers. Alternatively, the trousers may be supplied without closures for exclusive use with these covers.

Certain models of the trousers are made of transparent material to permit observation of skin color, bleeding wounds, and the like. The covers may be fabricated of a transparent plastic film to permit unobscured observation with this type of trousers.

Certain trousers provide access ports along the spine and detaching means at the joining of legs and abdominal portion. These are generally used to provide access to the patient for spinal fluid and femoral artery sampling. The covers may be fabricated of a plastic film that is easily punctured or cut to provide access for these functions.

Figure 11:
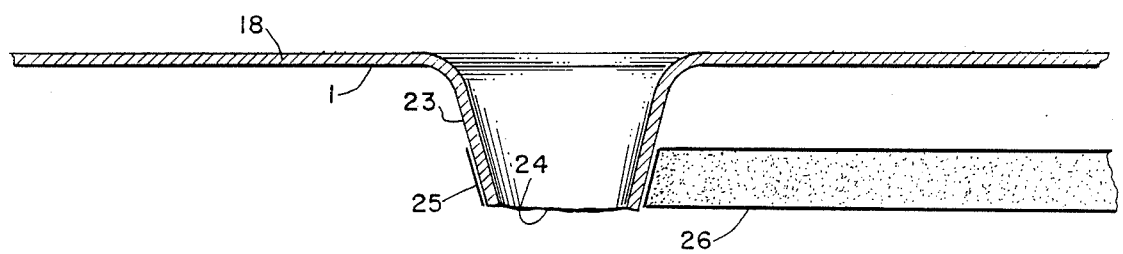
FIG. 11 shows a cross sectional detail of the aperture and sealing means for the inflation tubes.

The gas tubes 14 for inflating the gas chambers pass from the trousers through the cover 1 via tubular apertures shown in the details of FIG. 11. The tubulation 23 is formed by molding the film of the cover into a cone, cutting an opening 24 and encircling the remaining cone with a cuff 25 of vinyl tape, leaving a strip of tape 26. When the trousers are inserted in the cover, the inflating tube is passed through the aperture 24 and the remaining vinyl strip 26 is wrapped tightly around cuff 26 and the tube to make a simple but tight seal.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

What is claimed is:

1. A disposable contamination-control cover for reusable inflatable trousers, comprising:
   a. a totally enclosing, impermeable cover means having an inner surface for affixing to said trousers and an outer surface for exposure to potentially contaminating environment;
   b. a large, sealable opening in said cover means for inserting said trousers for use and removing said trousers after use;
   c. a plurality of first fastening means attached to said inner surface for engaging said trousers at selected regions for firmly affixing said cover to said trousers;
   d. a plurality of second fastening means attached to said outer surface for firmly securing said trousers in covered condition around the body of a patient prior to inflating said trousers;
   e. sealable aperture means connected to said cover means for passing at least one gas-inflating tube connected to inflatable chambers in said trousers through said cover means so that said trousers may be inflated by gas inflating means external to said cover.

2. In the invention of claim 1, said cover means composed of plastic film.

3. In the invention of claim 2, said cover means composed of transparent plastic film.

4. In the invention of claim 1, said large, sealable opening having Ziploc type sealant.

5. In the invention of claim 1, said large, sealable opening having adhesive type sealant.

6. In the invention of claim 1, said first fastening means having hook and loop type fasteners.

7. In the invention of claim 7, said fasteners having removable protective cover strips to facilitate insertion of said trousers without interference from said fasteners.

8. In the invention of claim 1, said first fastening means having pressure sensitive adhesive type fasteners.

9. In the invention of claim 8, said fasteners having removable protective cover strips to facilitate insertion of said trousers without interference from said fasteners.

10. In the invention of claim 1, said second fastening means having hook and loop type fasteners.

11. In the invention of claim 1, said second fastening means having pressure sensitive adhesive type fasteners.

12. In the invention of claim 11, said fasteners having removable cover strips.

13. In the invention of claim 1, said aperture means including a substantially tubular portion extending from the surface of said cover means, said tubular portion including aperture sealing means for sealing said tubular portion tightly to said gas inflating tube to prevent contamination of said trousers.

14. In the invention of claim 13, said tubular portion formed from the material of said cover means.

15. In the invention of claim 13, said aperture sealing means including a strip of resilient adhesive tape with a portion wrapped around said tubulation to form a cuff to stabilize said tubular portion.

16. In the invention of claim 1, said cover means composed of a plastic film that can be easily cut to provide access to said patient.

* * * * *